(12) United States Patent
Zaiki

(10) Patent No.: US 7,341,375 B2
(45) Date of Patent: Mar. 11, 2008

(54) X-RAY DIAGNOSIS APPARATUS

(75) Inventor: Ryuji Zaiki, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/665,502

(22) Filed: Sep. 22, 2003

(65) Prior Publication Data

US 2004/0125920 A1 Jul. 1, 2004

(30) Foreign Application Priority Data

Sep. 20, 2002 (JP) ............................ P2002-274860

(51) Int. Cl.
*H05G 1/02* (2006.01)
(52) U.S. Cl. .................. 378/196; 378/197; 378/209
(58) Field of Classification Search .................. 378/20, 378/195–198, 114–118, 208, 209
See application file for complete search history.

(56) References Cited

U.S. PATENT DOCUMENTS

| | | | | |
|---|---|---|---|---|
| 4,298,801 A | * | 11/1981 | Heitman et al. ............ 378/196 |
| 5,561,699 A | * | 10/1996 | Fenner ........................ 378/208 |
| 6,131,690 A | * | 10/2000 | Galando et al. ............ 378/198 |
| 6,801,594 B1 | * | 10/2004 | Ali et al. ........................ 378/4 |
| 6,950,496 B2 | * | 9/2005 | Zimmermann et al. ..... 378/116 |
| 7,079,022 B2 | * | 7/2006 | Kagermeier et al. ........ 340/514 |
| 7,256,705 B2 | * | 8/2007 | Kagermeier et al. ... 340/825.72 |

FOREIGN PATENT DOCUMENTS

JP 2001-46365 2/2001

* cited by examiner

*Primary Examiner*—Jurie Yun
(74) *Attorney, Agent, or Firm*—Oblon, Spivak, McClelland, Maier & Neustadt, P.C.

(57) ABSTRACT

An X-ray diagnosis apparatus includes a wireless communication unit that transmits a signal related to the drive of at least one of a supporting unit and a bed from an operation unit to the bed. The X-ray diagnosis apparatus may include a state detection unit that detects a state of attachment of an operation unit to a bed. The apparatus is controlled by detecting a position of the operation unit; detecting an operation direction of the operation unit; determining a drive direction based on the position of the operation unit and the operation direction of an operation unit; and driving at least one of the bed and the supporting unit in the determined drive direction.

17 Claims, 15 Drawing Sheets

X-RAY DIAGNOSIS APPARATUS

CROSS-REFERENCE TO RELATED APPLICATIONS

This application is based upon and claims the benefit of priority from prior Japanese Patent Application No. P2002-274,860 filed on Sep. 20, 2002, the entire contents of which are incorporated herein by reference.

FIELD OF THE INVENTION

The present invention is related to an X-ray diagnosis apparatus that irradiates X-ray to an object, and detects the X-ray penetrated through the object to perform fluoroscopy and radiography inside the object.

BACKGROUND OF THE INVENTION

FIG. 1 is a side view of a conventional X-ray diagnosis apparatus. The X-ray diagnosis apparatus includes a plate 111 on which a patient P is put, a bed body 112 which holds and moves the plate 111, an X-ray tube 113 which irradiates X-ray to the patient P, an X-ray detector 114 which detects X-ray penetrated through the patient P, and a supporting unit 115 which supports and moves the X-ray tube 113 and the X-ray detector 114. The X-ray diagnosis apparatus further includes an operation panel 116 used for operating drive of the bed body 112 or the supporting unit 115, a monitor 117 which displays an image created by an image processor based on the detection result from the X-ray detector 114, and a controller which controls the drive of the bed body 112 or the supporting unit 115. The bed body 112 moves the plate 111 in a tilt direction centering on a rotation center O of the plate 111, a vertical direction, a longitudinal direction indicated as a dotted arrow a shown in FIG. 1, a short direction (depth direction in FIG. 1), and a rolling direction. The supporting unit 115 rotates the X-ray tube 113 and the X-ray detector 114 according to the angle of the tilt direction centering on an interested part Q, such that the X-ray is irradiated to several directions. In more detail, the supporting unit 115 moves in a longitudinal rotation direction indicated as an arrow b shown in FIG. 1, in a slide rotation direction that is on a vertical face in a plane including the X-ray tube and X-ray detector, and in a main rotation direction that is on a horizontal face about an axis intersecting the X-ray tube and the X-ray detector. The supporting unit 115 further moves in the horizontal direction indicated as an arrow c in FIG. 1, when the patient P is put on the plate 111.

As shown in FIG. 2, the operation panel 116 including a cable W is attached to the bed body 112. For example, the operation panel 116 can be attached to both sides of the bed body 112 (Position A and B) via guide rails, and it is possible to operate the drive of the bed body 112 and the supporting unit 115 from both sides (Direction α and β) of the plate 111. As another example, the operation panel 116 can be selectively mounted on a head side or a leg side of the plate 111. As further example, the operation panel 116 is put on a movable seat 1112, as shown in FIG. 3. The operation panel 116 is connected to the bed body 112 via a cable W. The operation panel 116 is selectively positioned on both sides of the bed body 112 in order to operate the drive of the bed body 112 and the supporting unit 115 as well as FIG. 2. In also this case, the operation panel 116 can be selectively positioned on a head side or a leg side of the plate 111.

Japanese Patent Publication (Kokai) No. 2001-46365 (column 0019-0029 and FIG. 5 through FIG. 10) discloses an X-ray CT apparatus including a foot switch near the bed body 112 in order to start and stop the irradiation of the X-ray from the X-ray tube 113. The position of the foot switch may be changed as well as the operation panel 116. In this X-ray CT apparatus, the position of the foot switch is changed according to a position of an operator or a position to avoid mis-operation.

As shown in FIG. 2 and FIG. 3, since the operation panel 116 is connected to the bed body 112 via the cable W, the cable W can interfere when the patient P is put on the plate 111 or the position of the operation panel 111 is changed to perform IVR. Therefore, the operator has to be careful to handle the cable W and not be caught by the cable W.

In addition, a relation between an operation direction of the operation panel 116 and a driving direction of the bed body 112 and the supporting unit 115 becomes different when the operation panel 116 is mounted on one side or the other side of the bed body 112, because the operation direction becomes reverse. For example, when the operation panel 116 is mounted on a position A and the operator tilts a operation lever 116a of the operation panel 116 in a right direction to move the supporting unit 115 in the right direction shown as an arrow c in FIG. 4, the supporting unit 115 moves in the right direction. In such a situation, when the position of the operation panel 116 is changed to opposite position B and the operator tilts the operation lever 116a in a right direction, the supporting unit 115 moves in a left direction. In this case, it is necessary for the operator to match the operation direction to the driving direction by using buttons on the operation panel 116. That is, the operator manually has to recognize the position of the operation panel 116 to set the relation between the operation direction and the driving direction.

Thus, in the conventional X-ray diagnosis apparatus, it is necessary for the operator to be careful to handle the cable when the position of the operation panel 116 is changed, and/or it is necessary for the operator to manually set the relation between the operation direction and the driving direction.

SUMMARY OF THE INVENTION

One object of the present invention is to ameliorate the above-mentioned problems.

To that end, according to one aspect of the present invention, there is provided an X-ray diagnosis apparatus, including a supporting unit configured to support to an X-ray tube that irradiates X-ray to an object and an X-ray detector that detects X-ray penetrated through the object; a bed configured to have the object placed thereon; an operation unit configured to operate drive of at least one of the supporting unit and the bed; a wireless communication unit configured to transmit a wireless signal related to the drive from the operation unit to the bed; and a drive control unit configured to control the drive of at least one of the supporting unit and the bed based on the transmitted wireless signal.

According to another aspect of the present invention, there is provided an X-ray diagnosis apparatus, including a supporting unit configured to support to an X-ray tube that irradiates X-ray to an object and an X-ray detector that detects the X-ray penetrated through the object; a bed configured to have the object placed thereon; an operation unit configured to operate drive of at least one of the supporting unit and the bed and configured to be attached to and detached from a plurality of attachment units of the bed; a drive control unit configured to control the drive of at least one of the supporting unit and the bed based on the signal; and a state detection unit configured to detect a state of attachment of the operation unit to the bed.

According to a further aspect of the present invention, there is provided an X-ray diagnosis apparatus, including a supporting unit configured to support an X-ray tube that irradiates X-ray to an object and an X-ray detector that detects the X-ray penetrated through the object; a bed configured to have the object placed thereon; means for operating drive of at least one of the supporting unit and the bed; means for transmitting a signal related to the drive from the operation unit to the bed by wireless communication; and means for controlling the drive of at least one of the supporting unit and the bed based on the signal.

According to a further aspect of the present invention, there is provided a method for controlling an X-ray diagnosis apparatus including a supporting unit configured to support to an X-ray tube that irradiates X-ray an object and an X-ray detector that detects the X-ray penetrated through the object, a bed configured to have the object placed thereon, and an operation unit configured to operate drive of at least one of the supporting unit and the bed, wherein the method includes detecting a position of the operation unit; detecting an operation direction of the operation unit; determining a drive direction based on the position of the operation unit and the operation direction of an operation unit; and driving at least one of the bed and the supporting unit in the determined drive direction.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. In the drawings.

DETAILED DESCRIPTION OF THE INVENTION

Figure 1:
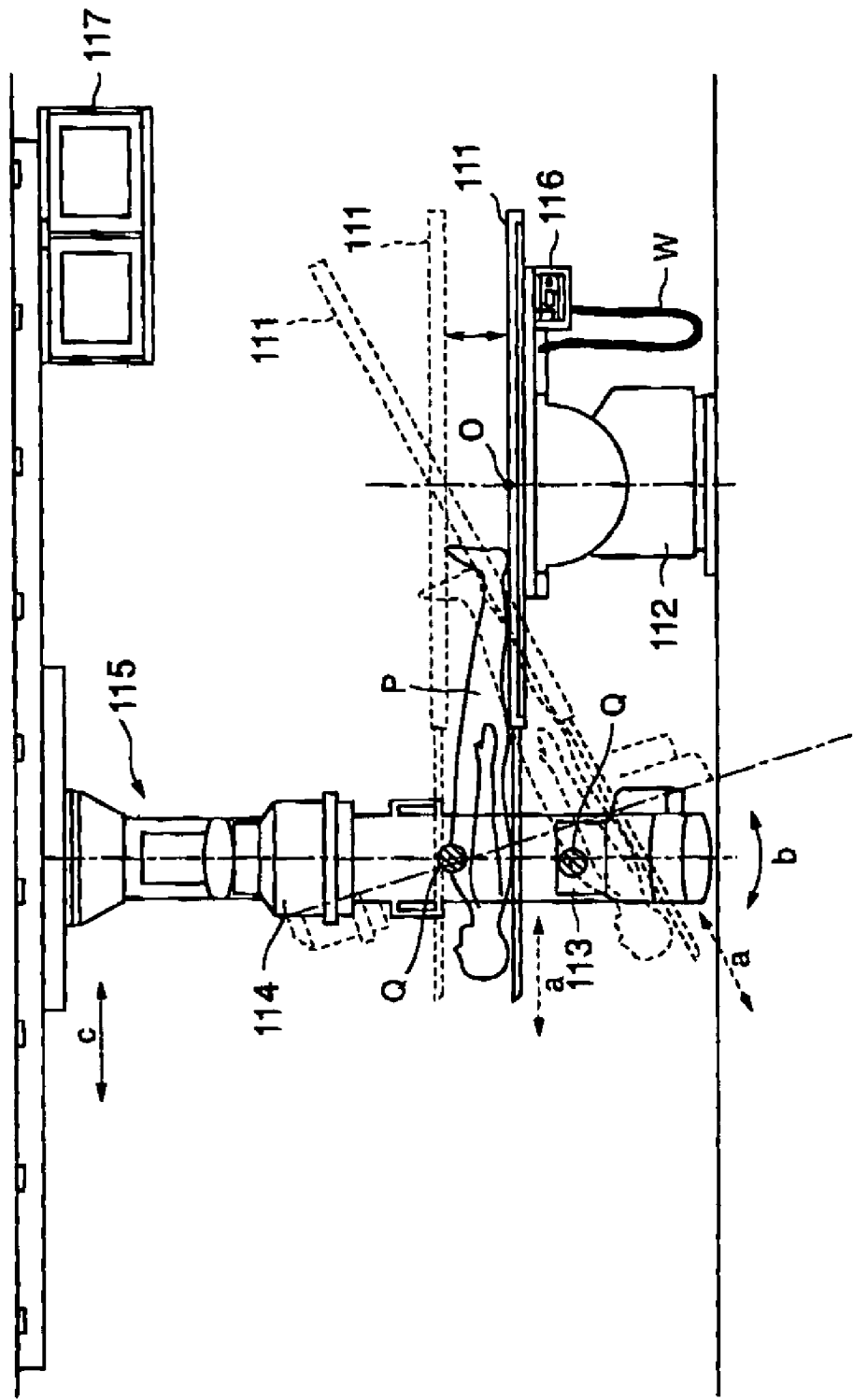
FIG. 1 is a side view of a conventional X-ray diagnosis apparatus.
Figure 2:
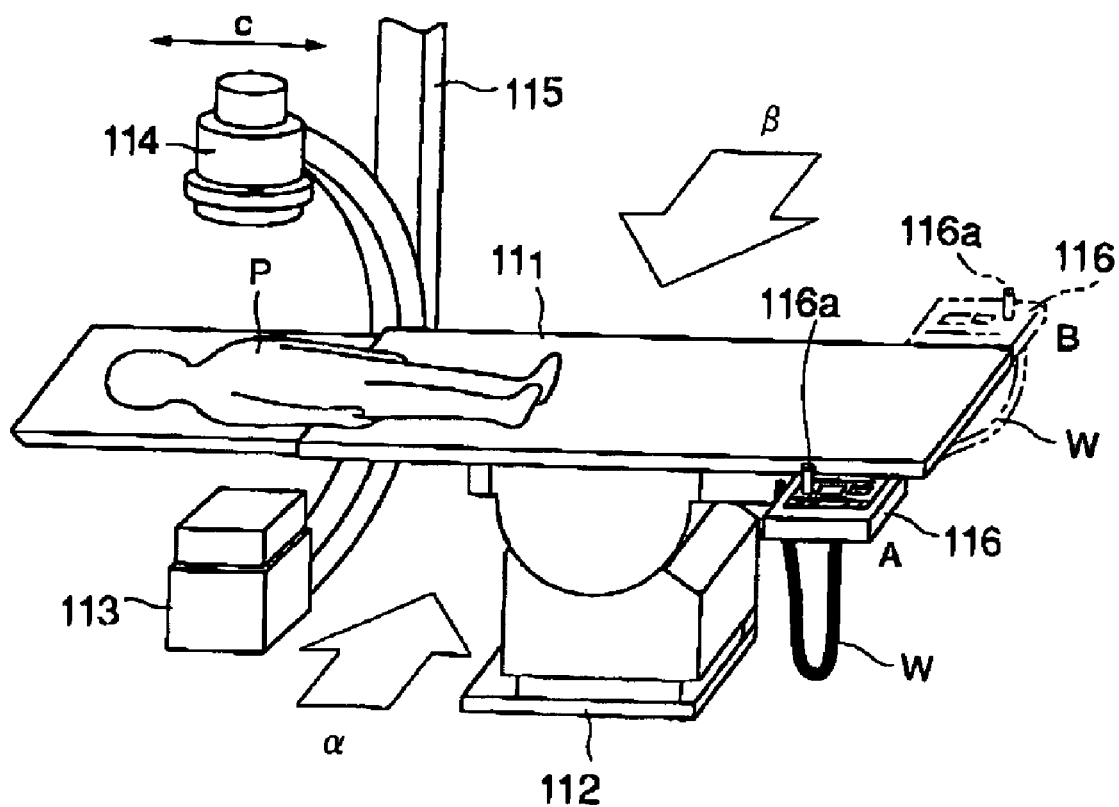
FIG. 2 is a perspective view of the conventional X-ray diagnosis apparatus.
Figure 3:
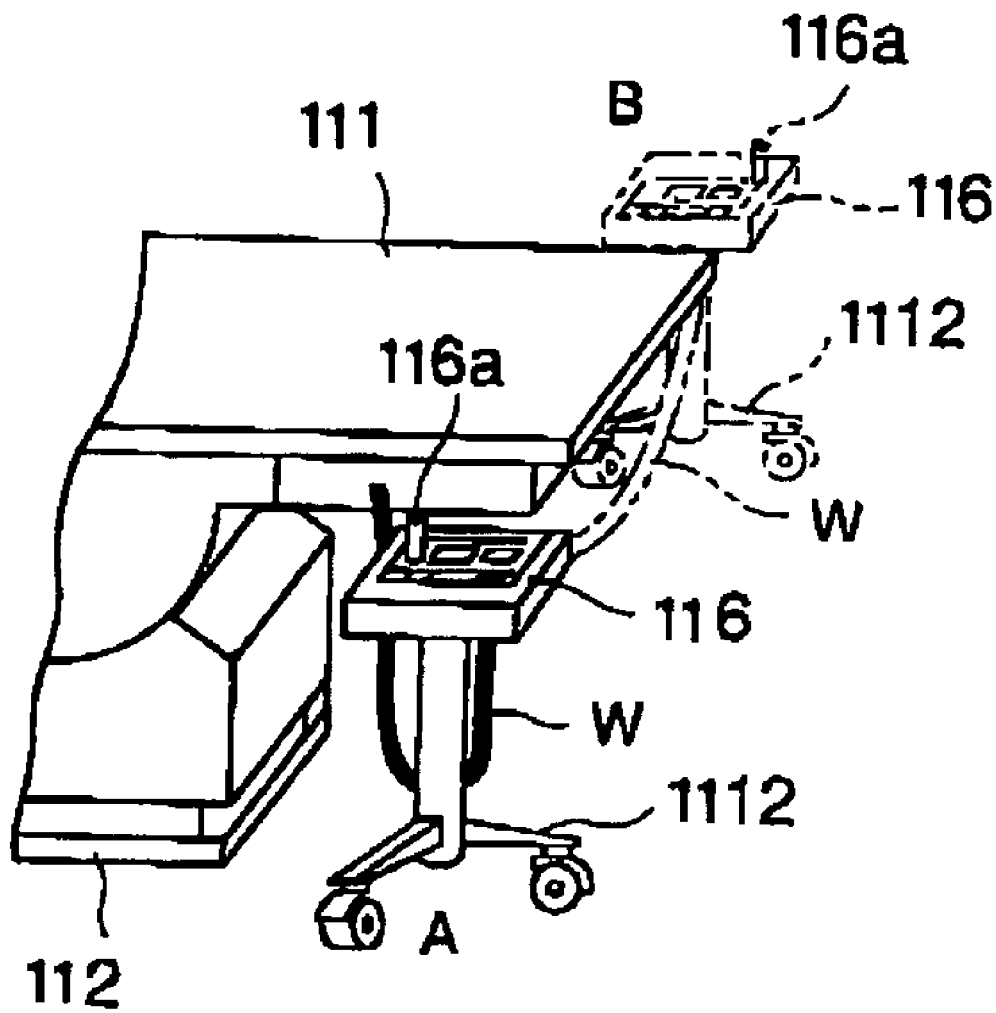
FIG. 3 is a partial perspective view of another conventional X-ray diagnosis apparatus.

Referring now to the drawings, wherein like reference numerals designate the same or corresponding parts throughout the several views, a first embodiment of an X-ray diagnosis apparatus is explained with reference to FIG. 4, which is a side view of the X-ray diagnosis apparatus. The X-ray diagnosis apparatus includes a plate 1 on which a patient P is put, a bed body 2 which holds and moves the plate 1, an X-ray tube 3 which irradiates X-ray to the patient P, an X-ray detector 4 which detects the X-ray penetrated through the patient P, and a supporting unit 5 which supports and moves the X-ray tube 3 and the X-ray detector 4. The X-ray diagnosis apparatus further includes an operation panel 6 used for operating drive of the bed body 2 or the supporting unit 5, a monitor 7 which displays the image created by an image processor based on the detection result from the X-ray detector 4, a high-voltage generation unit which applies high-voltage to the X-ray tube 3, and a controller which controls the drive of the bed body 2 or the supporting unit 5. The image processor, the high-voltage and the controller will be explained below.

Figure 4:
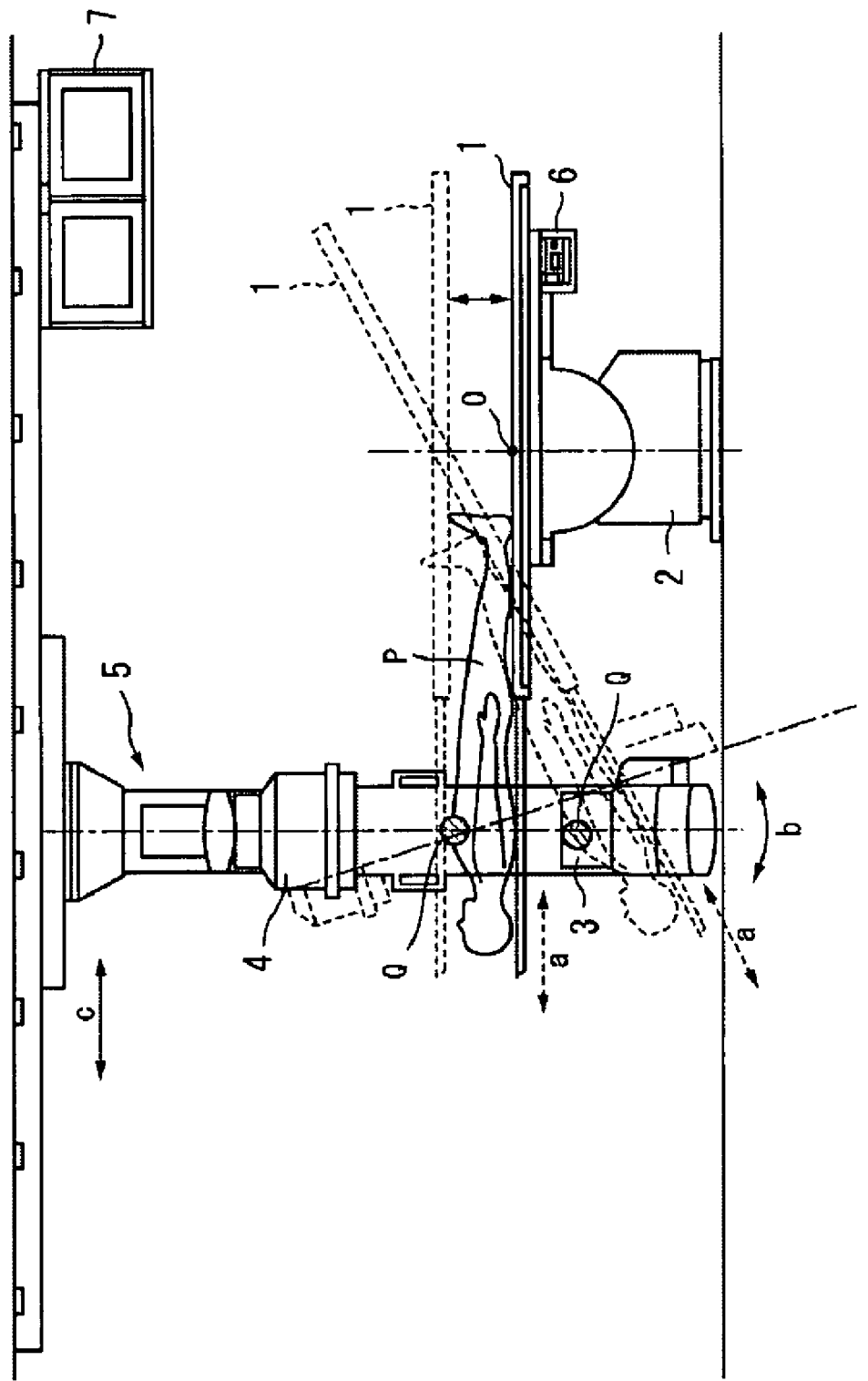
FIG. 4 is a side view of an X-ray diagnosis apparatus of a first embodiment.

The bed body 2 moves the plate 1 in a tilt direction centering on a rotation center O of the plate 1, a vertical direction, a longitudinal direction indicated as a dotted arrow a shown in FIG. 4, and a short direction (depth direction in FIG. 4), and a rolling direction. The supporting unit 5 rotates the X-ray tube 3 and the X-ray detector 4 according to the angle of the tilt direction centering on an interested part Q, such that the X-ray is irradiated in several directions. In more detail, the supporting unit 5 moves in a longitudinal rotation direction indicated as an arrow b shown in FIG. 4, in a slide rotation direction that is on a vertical face, and in a main rotation direction that is on a horizontal face. The supporting unit 5 further moves in the horizontal direction indicated as an arrow c in FIG. 4, when the patient P is put on the plate 1.

Figure 5:
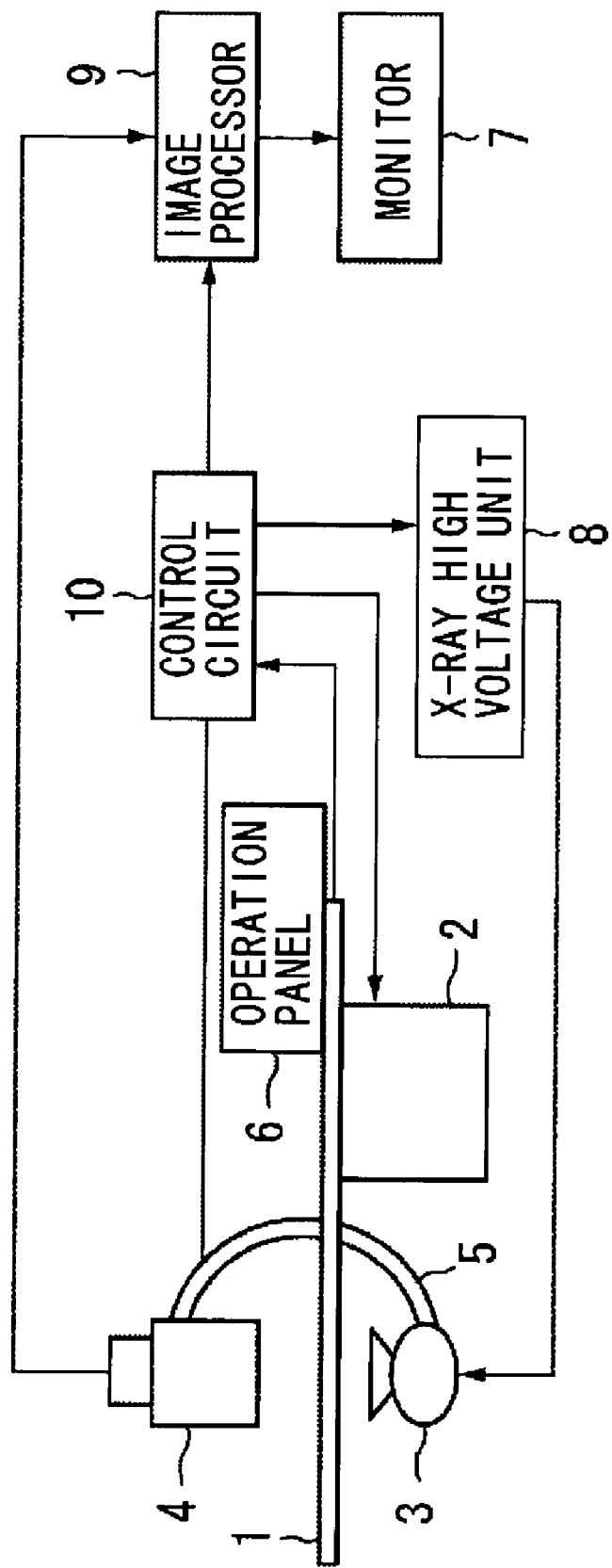
FIG. 5 is a block diagram of the X-ray diagnosis apparatus of the first embodiment.

A block diagram of electric composition of the X-ray diagnosis apparatus is shown in FIG. 5. The X-ray high-voltage unit 8 is connected to the X-ray tube 3, and the X-ray detector 4 is connected to the image processor 9 which creates an image based on the detection result from the X-ray detector 4. Moreover, the image processor 9 is connected to the monitor 7 which displays the image created by the image processor 9. The control circuit 10 which controls each part is connected to the bed body 2, the supporting unit 5, the operation panel 6, the X-ray high-voltage unit 8, and the image processor 9. The control circuit 10 controls the value of high-voltage applied to the X-ray tube 3 from the X-ray high-voltage unit 8, the various image processings performed by the image processor 9, and the drive of the bed body 2 or the supporting unit 5 based on control signals from the operation panel 6.

Figure 6:
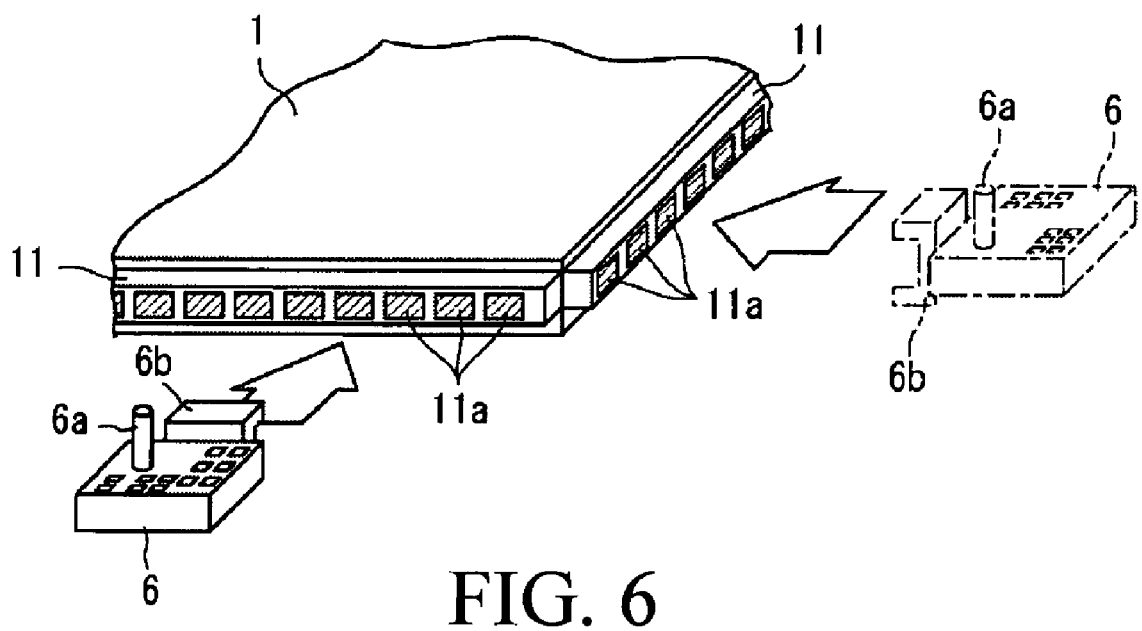
FIG. 6 is a partial perspective view of an operation panel and a plate of the X-ray diagnosis apparatus of the first embodiment.

The operation panel 6 and the plate 1 of the X-ray diagnosis apparatus is explained with reference to FIG. 6. The operation panel 6 includes an attachment part 6b attachable to a guide rail 11 which is an example of an attachment unit. The guide rail is placed on a side of the plate 1. The operation panel 6 may be attachable to each side of the plate 1. For example, when the plate 1 is rectangle, the operation panel 6 may be attachable to four side parts.

Figure 7:
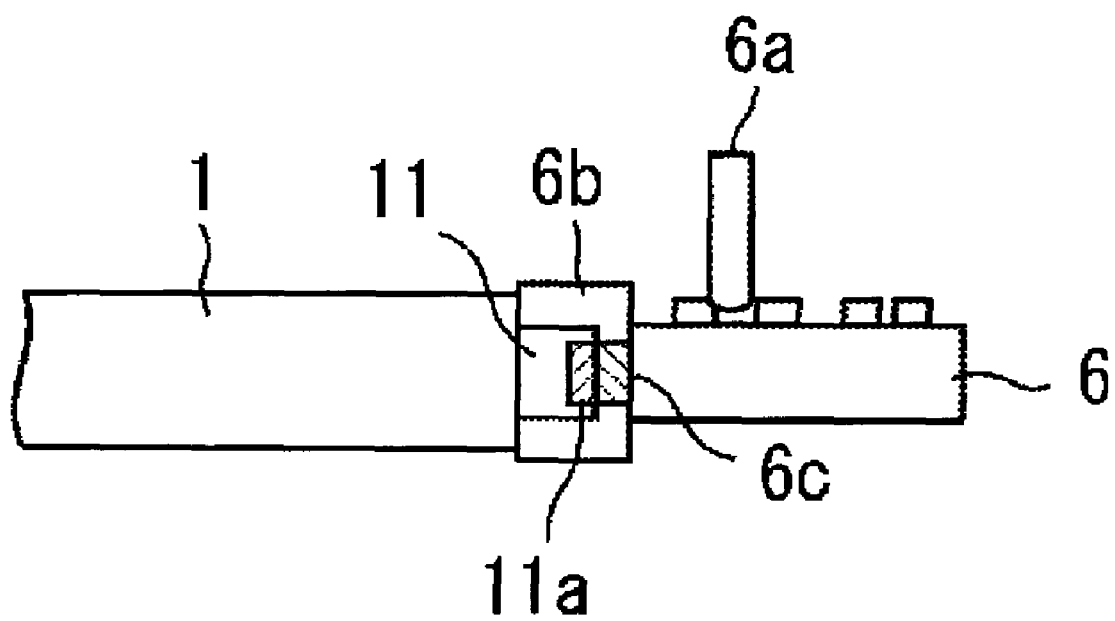
FIG. 7 is a partial sectional view of the operation panel and the plate of the X-ray diagnosis apparatus of the first embodiment.
Figure 8:
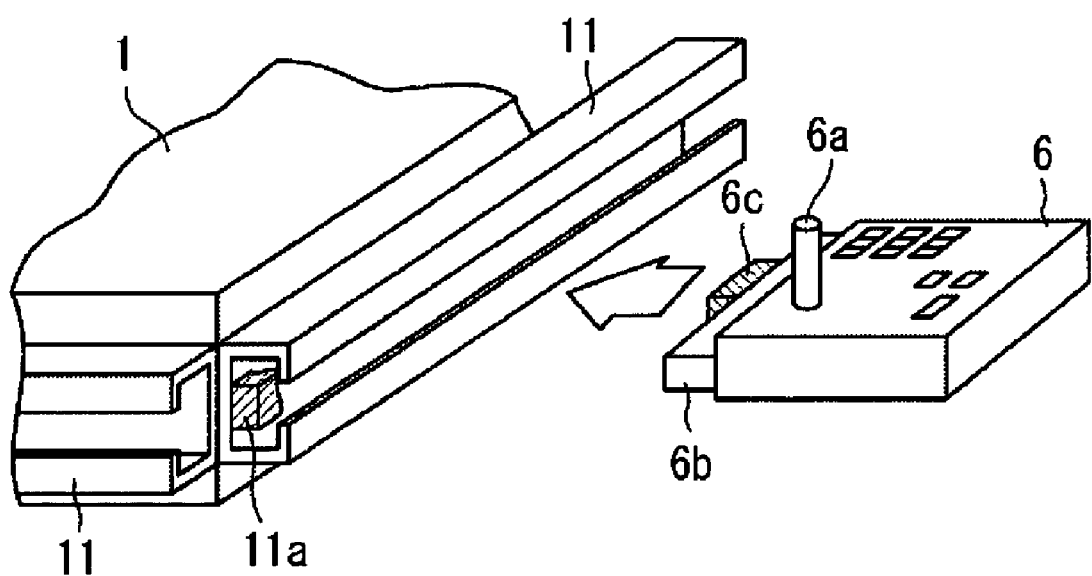
FIG. 8 is a partial perspective view of an operation panel and a plate of an X-ray diagnosis apparatus of another embodiment.
Figure 9:
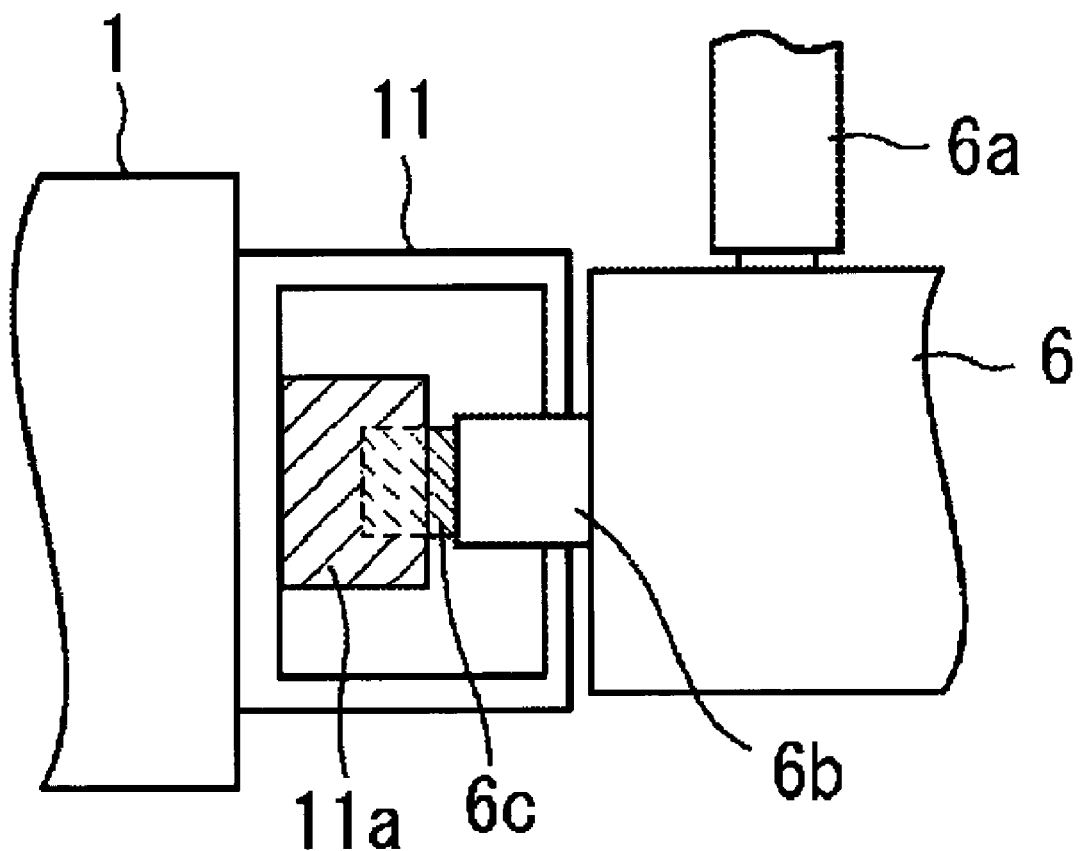
FIG. 9 is a partial sectional view of the operation panel and the plate of the X-ray diagnosis apparatus of another embodiment.

Furthermore, as shown in FIG. 7, a transmitting part 6c that transmits the information related to the operation of the operation panel 6 (hereinafter called as SW signal) on infrared rays, is placed on a face of the attachment part 6b of the operation panel 6. The guide rail 11 includes a receiving part 11a that receives the infrared rays from the operation panel 6 and is placed on a corresponding face to the transmitting part 6c. In the first embodiment, since the signal is transmitted and received by the infrared rays and a conventional signal cable can be omitted, it is easy to handle the operation panel 6. And it is also easy to attach or detach the operation panel 6. As shown in FIG. 6, the guide rail 11 may preferably include several equally positioned receiving parts 11a in order that the operation panel 6 is attachable to a whole part of the guide rail 11 of the plate 1. The receiving part 11a may be positioned inside of the guide rail 11 instead of outside of the guide rail 11. For instance, as shown in FIG. 8, an internal space is established in the guide rail 11, and the receiving parts 11a is positioned at the end of the guide rail 11. The transmitting part 6c sticks out to the internal space. As shown in FIG. 9, the receiving part 11a can receive the infrared rays, even if the operation panel 6 is attached to any parts of the guide rail 11. In such a structure the receiving part 11a can be provided with respect to each guide rail, and it is possible to reduce to influence of dust, exogenous material, and outside light, etc. However, in order to shorten the communication distance between the receiving part 11a and the transmitting part 6c to establish accurate infrared communication, it is preferable that the receiving part 11a is positioned outside of the guide rail 11. Either structure can be employed.

When a wireless communication, such as the infrared communication and not a cable communication, is used, it may be performed to check establishment of the communication or to check error of the SW signal, in order to detect break of various switch systems in the operation panel 6, incorrect recognition due to noise during communication, and/or other communication fault. For this reason, the control circuit 10 may control the receiving part 11a to perform the communication several times to confirm the SW signal, and if the communication is not appropriately established, a safety action, such as stop of drive of the bed body 2 and the supporting unit 5, may be implemented.

Figure 10:
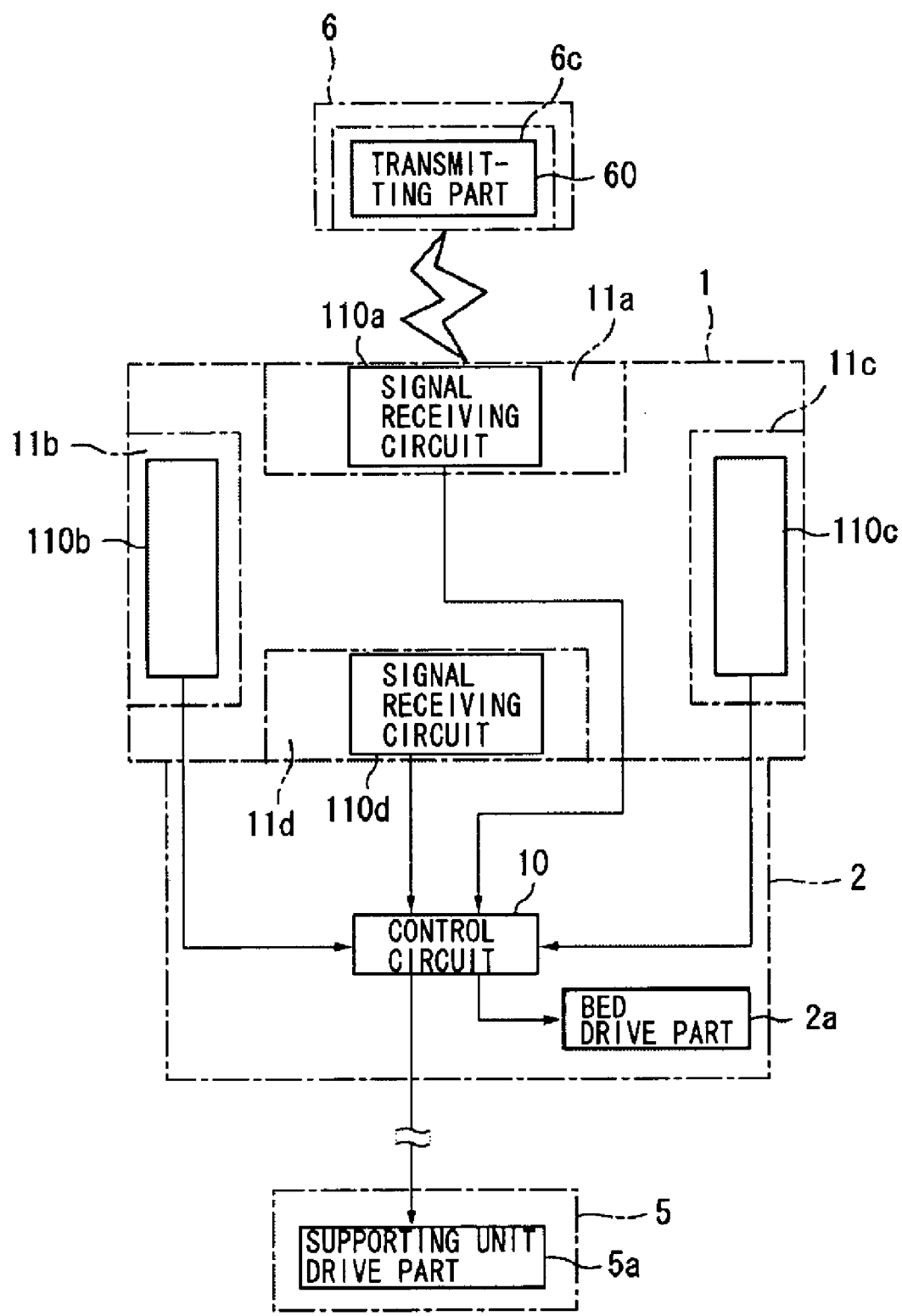
FIG. 10 is a block diagram of the plate and a bed body of the X-ray diagnosis apparatus of the first embodiment.
Figure 11:
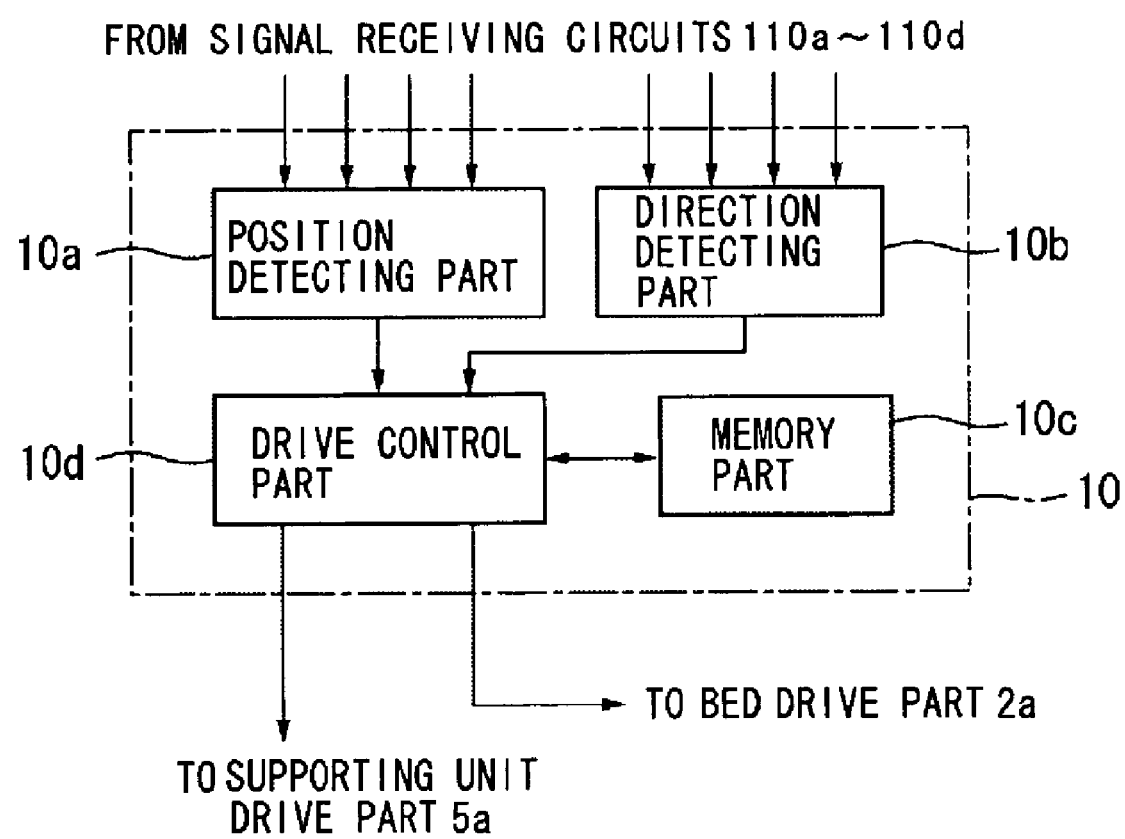
FIG. 11 is a block diagram of a control circuit of the X-ray diagnosis apparatus of the first embodiment.

A detail of processing, in the control circuit 10, for matching an operation direction of the operation panel 6 and a driving direction of the bed body 2 and the supporting unit 5 according to attachment position of the operation panel 6 attached to the side of the plate 1, is explained. In FIG. 10 and FIG. 11, the infrared communication between the operation panel 6 and plate 1 is shown. The transmitting part 6c of the operation panel 6 includes a signal transmitting circuit 60 which transmits the SW signal. Receiving parts 11a through 11d that are placed at the guide rails on sides of the plate 1, such as head, right, left and leg sides, respectively include signal receiving circuits 110a through 110d that receive the SW signal transmitted from the signal transmitting circuit 60. The signal receiving circuits 110a-110d of the plate 1 are connected to the control circuit 10 in the bed body 2, and the control circuit 10 is connected to a bed drive part 2a for driving the bed body 2 and a supporting unit drive part 5a for driving the supporting unit 5 supporting the X-ray tube 3 and the X-ray detector 4.

The control circuit 10 detects an attachment state of the operation panel 6, as shown in FIG. 11. For example, the control circuit 10 includes a position detecting part 10a that detects the attachment position of the operation panel 6 by detecting which signal receiving circuit receives the SW signal, and includes a direction detecting part 10b that detects the operation direction of an operation lever 6a based on the SW signal from the operation panel 6. The control circuit 10 further includes a memory part 10c that stores information of relation between the drive direction of the bed drive part 2a and the supporting unit drive part 5a and the operation direction of the operation lever 6a, and includes a drive control part 10d determines the drive direction based on the position of the operation panel 6 and the operation direction of an operation lever 6a, referring to the information of the relation stored in the memory part 10c.

Figure 12:
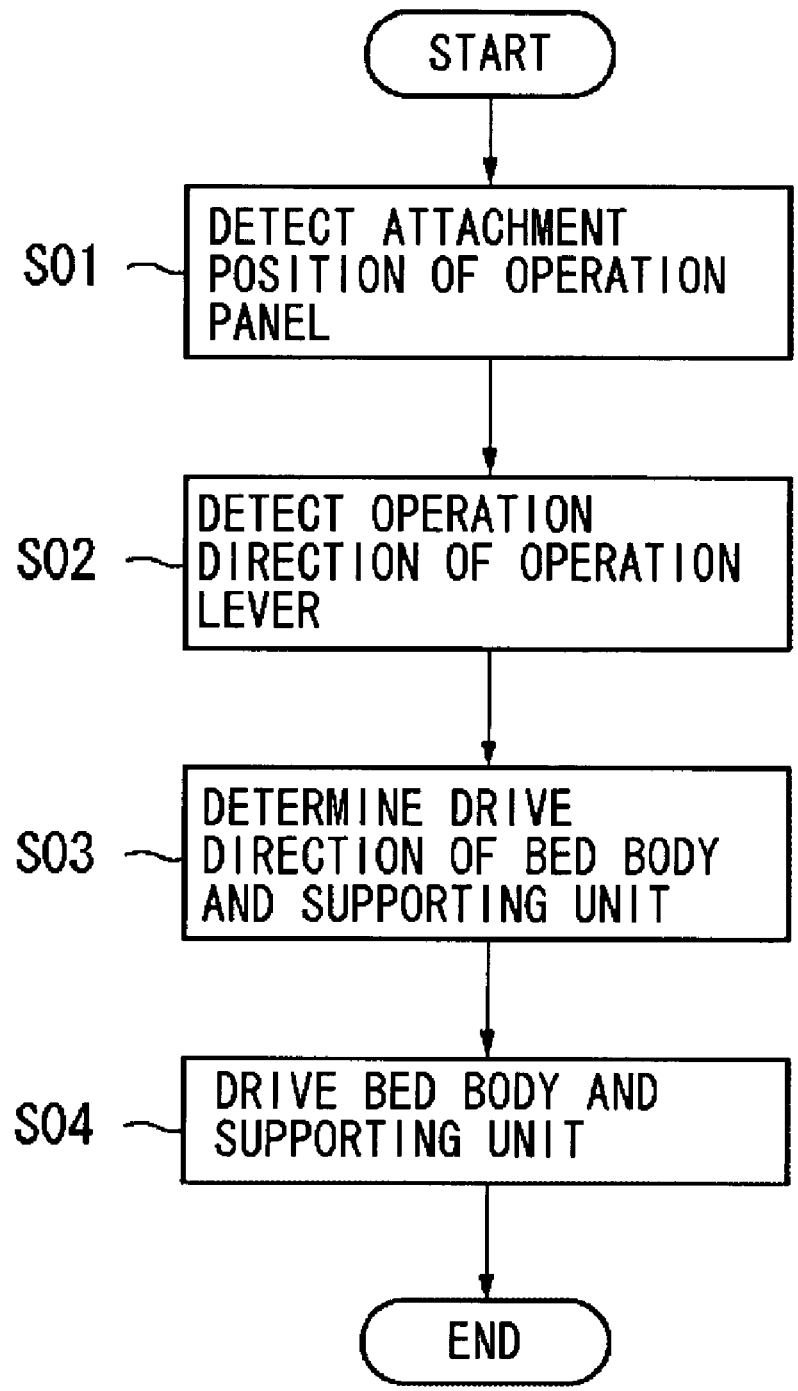
FIG. 12 is a flow chart of an operation of the control circuit of the X-ray diagnosis apparatus of the first embodiment.

Operation of the control circuit 10 is explained with reference to FIG. 12. When the operation panel 6 is attached to one of the guide rails 11 and the operation lever 6a of the operation panel 6 is operated, the SW signal is generated. The position detecting part 10a detects the attachment position of the operation panel 6 by detecting which signal receiving circuit receives the SW signal (S01). The direction detecting part 10b detects the operation direction of the operation lever 6a based on the SW signal from one of the signal receiving circuits 110a through 110d (S02). The drive control part 10d determines the drive direction based on the position of the operation panel 6 and the operation direction of an operation lever 6a, referring to the information of the relation stored in the memory part 10c (S03). The bed body 2 and the supporting unit 5 are moved based on the determined drive direction (S04). For example, when the position of the operation panel 6 is changed from the right side to the left side in the short direction of the plate 1, the drive directions of the bed drive part 2a and the supporting unit drive part 5a are reversed in both short and longitudinal directions. In another example, when the position of the operation panel 6 is changed from the down side to the left side, the drive directions of the bed drive part 2a and the supporting unit drive part 5a are reversed with respect to each other.

As described above, in the first embodiment, since infrared communication is performed between the operation panel 6 and the plate 1, it is possible to omit the conventional cable and it is easy for the operator to attach or detach the operation panel 6 to the plate 1.

Figure 13:
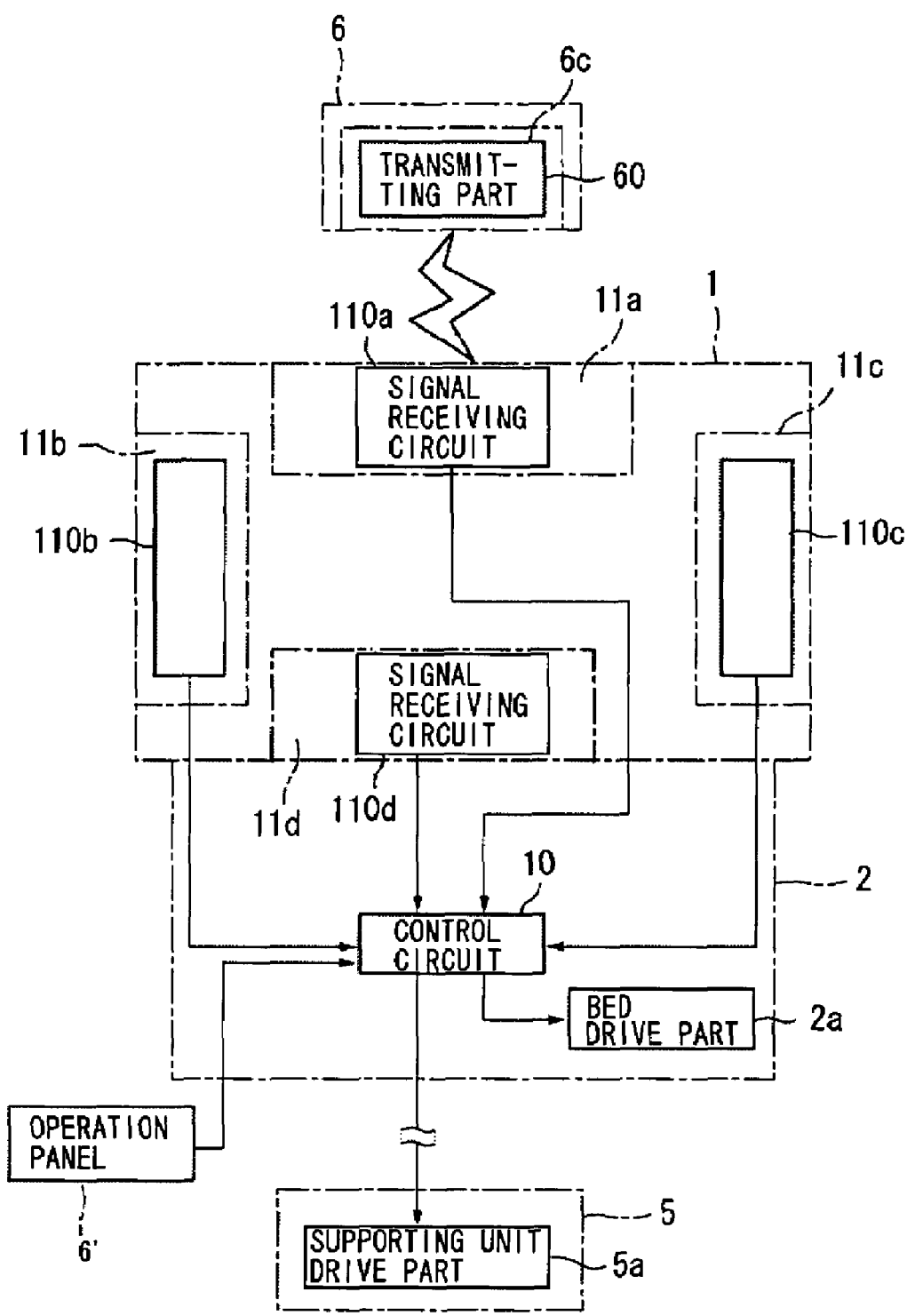
FIG. 13 is a block diagram of the plate and a bed body of the X-ray diagnosis apparatus of another embodiment.
Figure 14:
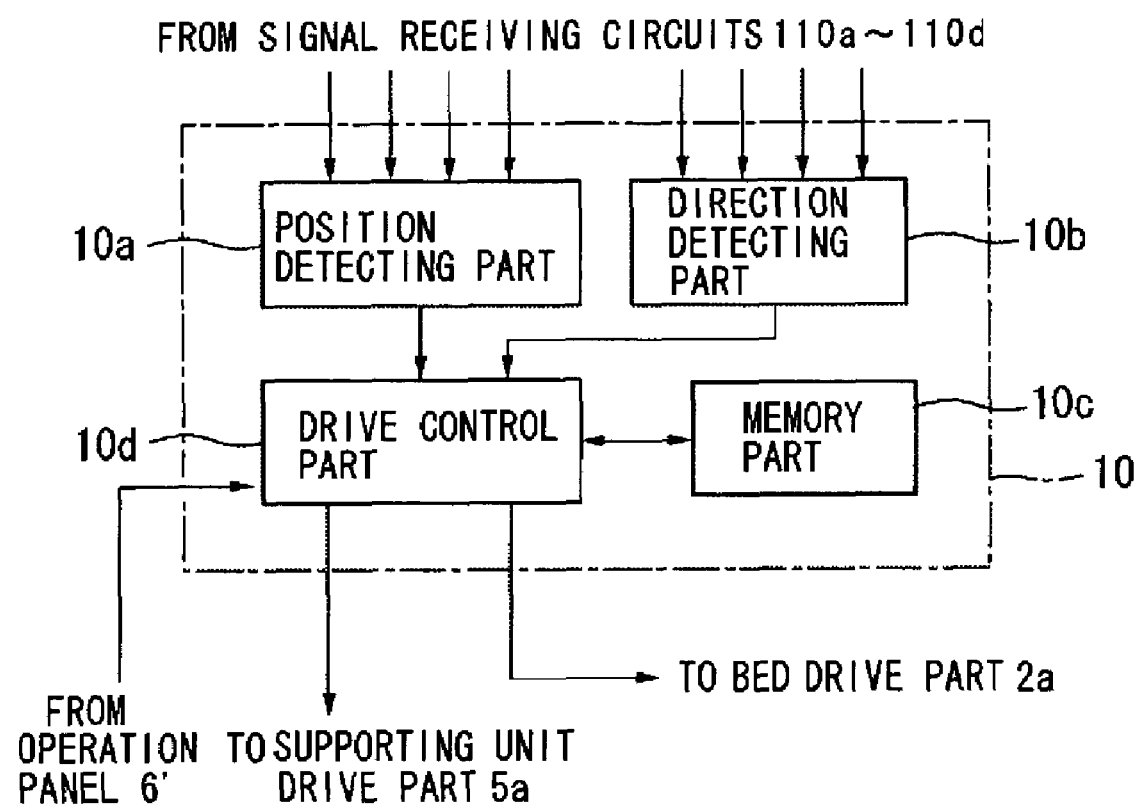
FIG. 14 is a block diagram of a control circuit of the X-ray diagnosis apparatus of another embodiment.
Figure 15:
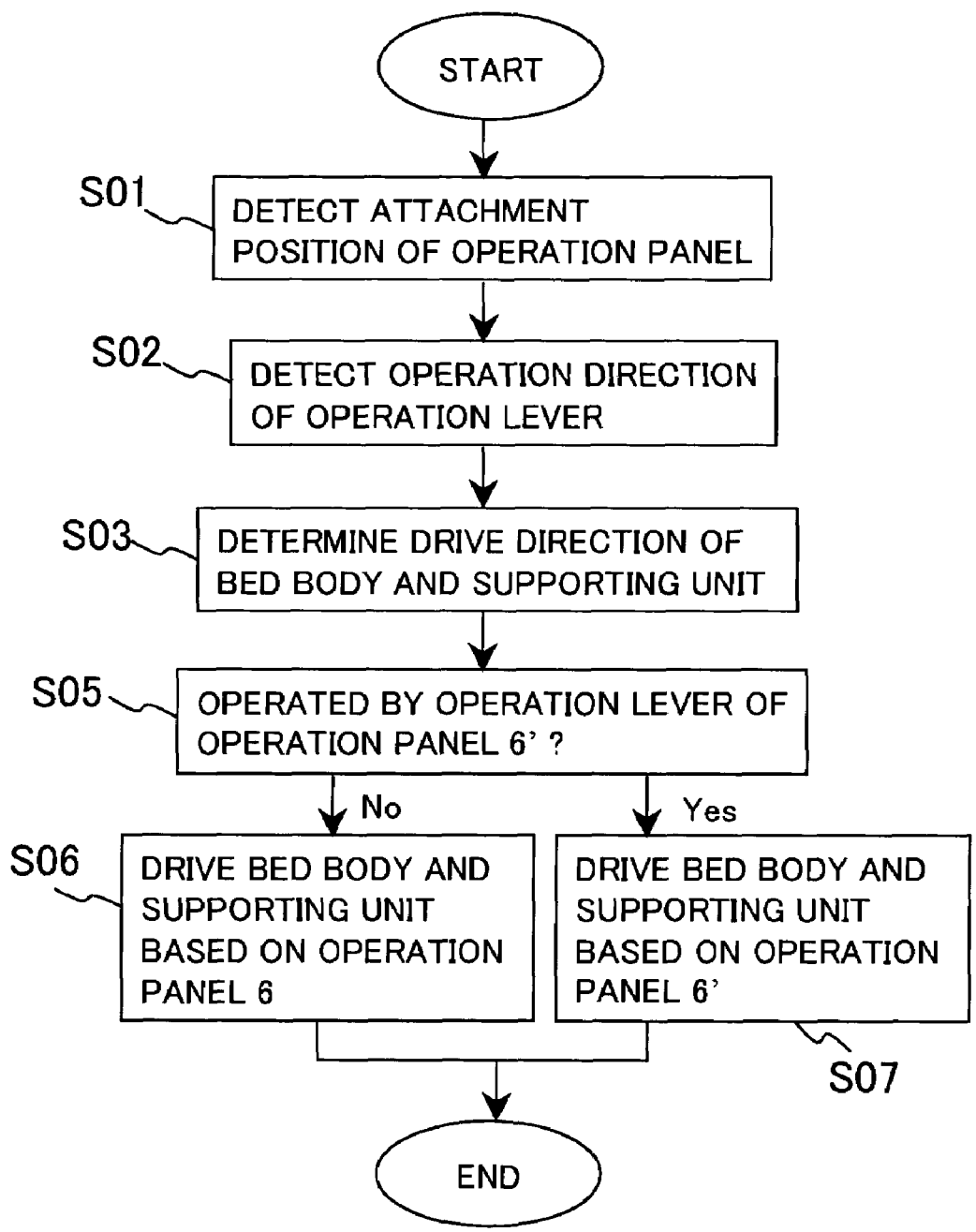
FIG. 15 is a flow chart of an operation of the control circuit of the X-ray diagnosis apparatus of another embodiment.

A second embodiment of an X-ray diagnosis apparatus is explained with reference to FIG. 13 through FIG. 15. To simplify the explanation, the explanation of elements of the second embodiment common with the first embodiment are omitted. In the second embodiment, in addition to the operation panel 6 which performs the infrared communication as in the first embodiment, an operation panel 6' which performs cable communication is provided. The operation panel 6' is connected to the control circuit 10. An operation of the communication between the operation panel 6' and the plate1 is performed in steps S01 to S03 as shown in FIG. 15 as well as the first embodiment. In step S05, the control circuit 10' detects an operation of the operation panel 6'. When the operation panel 6' is not operated by the operator, the bed body 2 and the supporting unit 5 are driven based on the operation panel 6 (S06). When the operation panel 6' is operated by the operator, the bed body 2 and the supporting unit 5 are driven by priority based on the operation panel 6', regardless of the operation of the operation panel 6 (S07). In the second embodiment, since the operation panel 6' can be used in case the infrared communication does not work well, safety improves.

The present invention is not limited to the above embodiments, and various modifications may be made without departing from the spirit or scope of the general inventive concept. For example, not both but one of the bed body 2 and the supporting unit 5 may be driven with the operation panel 6. The plate 1 may be driven with the operation panel 6. Moreover, the operation panel 6 may be attachable only to both sides of the plate 1 not to whole sides. The operation panel 6 may be attachable to the bed body 2. The communication of the SW signal between the operation panel 6 and the plate 1 may be performed by other wireless communication methods, such as electric wave instead of the infrared communication method. The position of the operation panel 6 may be detected by a detector using GPS and earth magnetism, etc. As another example of detection of the attachment state, it may be detected whether at least one signal receiving circuit receives the SW signal. When the SW is not detected, it is determined that the operation panel 6 is not appropriately attached to the plate, and the bed body 2 and the supporting unit 5 may be stopped. Furthermore, as long as the state of the attachment is detected, a connector may be used to transmit the SW signal from the operation panel 6 to the bed body 2 instead of the infrared communication. The connector may be also used as the attachment unit instead of the guide rail 11. Moreover, a operation button may be used instead of the operation lever 6a.

Various additional modifications and variations are possible. It is therefore to be understood that within the scope of the appended claims, the present invention may be practiced differently than as specifically described herein.

What is claimed is:

1. An X-ray diagnosis apparatus, comprising:
   an X-ray tube that irradiates X-rays to an object and an X-ray detector that detects X-rays penetrated through the object;
   a supporting unit configured to support the X-ray tube and the X-ray detector;
   a bed configured to have the object placed thereon;
   an operation unit configured to define movement of at least one of the supporting unit and the bed;
   a state detection unit configured to detect a state of attachment of the operation unit to the bed;
   a wireless communication unit configured to transmit a wireless signal related to the movement from the operation unit to the bed;
   a drive control unit configured to control the movement of at least one of the supporting unit and the bed based on the transmitted wireless signal; and
   a plurality of attachment units configured to attach and detach the operation unit to the bed,
   wherein the drive control unit stops the movement of at least one of the supporting unit and the bed when the operation unit is not attached to any of the attachment units.

2. The X-ray diagnosis apparatus according to claim 1, wherein the state detection unit is configured to detect whether the operation unit is attached to at least one of the attachment units.

3. The X-ray diagnosis apparatus according to claim 1, wherein the state detection unit identifies the attachment unit of the plurality of attachment units to which the operation unit is attached.

4. The X-ray diagnosis apparatus according to claim 3, wherein the drive control unit controls a direction of the movement of at least one of the supporting unit and the bed based on a position of the identified attachment unit.

5. The X-ray diagnosis apparatus according to claim 1, wherein the attachment units include a guide rail.

6. The X-ray diagnosis apparatus according to claim 5, wherein the communication unit is provided with respect to the guide rail.

7. The X-ray diagnosis apparatus according to claim 1, wherein the communication unit transmits the wireless signal related to the movement several times.

8. The X-ray diagnosis apparatus according to claim 1, wherein the drive control unit controls the movement of at least one of the supporting unit and the bed in a horizontal direction.

9. The X-ray diagnosis apparatus according to claim 1, wherein the drive control unit controls the movement of at least one of the supporting unit and the bed in a rotation direction.

10. An X-ray diagnosis apparatus, comprising:
    an X-ray tube that irradiates X-rays to an object and an X-ray detector that detects X-rays penetrated through the object;
    a supporting unit configured to support the X-ray tube and the X-ray detector;
    a bed configured to have the object placed thereon;
    an operation unit configured to define movement of at least one of the supporting unit and the bed;
    a wireless communication unit configured to transmit a wireless signal related to the movement from the operation unit to the bed;
    a drive control unit configured to control the movement of at least one of the supporting unit and the bed based on the transmitted wireless signal;
    an attachment unit configured to attach and detach the operation unit to the bed;
    a second operation unit configured to define movement of at least one of the supporting unit and the bed; and
    a second communication unit configured to transmit a second signal related to the movement from the second operation unit to the bed by a cable,
    wherein the drive control unit controls the movement of at least one of the supporting unit and the bed based on the second signal transmitted by the cable prior to transmission of the wireless signal.

11. An X-ray diagnosis apparatus, comprising:
    an X-ray tube that irradiates X-rays to an object and an X-ray detector that detects X-rays penetrated through the object;
    a supporting unit configured to support the X-ray tube and the X-ray detector;
    a bed configured to have the object placed thereon;
    an operation unit configured to define movement of at least one of the supporting unit and the bed;
    a wireless communication unit configured to transmit a wireless signal related to the movement from the operation unit to the bed;
    a drive control unit configured to control the movement of at least one of the supporting unit and the bed based on the transmitted wireless signal;
    an attachment unit configured to attach and detach the operation unit to the bed;
    a second operation unit configured to define movement of at least one of the supporting unit and the bed; and
    a second communication unit configured to transmit a second signal related to the movement from the second operation unit to the bed by a cable, wherein the drive control unit stops the movement of at least one of the supporting unit and the bed when the second signal transmitted by the cable is different from the transmitted wireless signal.

12. An X-ray diagnosis apparatus, comprising:

an X-ray tube that irradiates X-rays to an object and an X-ray detector that detects the X-rays penetrated through the object;

a supporting unit configured to support the X-ray tube and the X-ray detector;

a bed configured to have the object placed thereon;

an operation unit configured to define movement of at least one of the supporting unit and the bed and configured to be attached to and detached from a plurality of attachment units of the bed;

a drive control unit configured to control the movement of at least one of the supporting unit and the bed based on a signal; and a state detection unit configured to detect a state of attachment of the operation unit to the bed.

13. The X-ray diagnosis apparatus according to claim 12, wherein the state detection unit is configured to detect whether the operation unit is attached to at least one of the attachment units.

14. The X-ray diagnosis apparatus according to claim 13, wherein the drive control unit is configured to stop the movement of at least one of the supporting unit and the bed when the operation unit is not attached to any of the attachment units.

15. The X-ray diagnosis apparatus according to claim 12, wherein the state detection unit is configured to identify the attachment unit to which the operation unit is attached.

16. The X-ray diagnosis apparatus according to claim 15, wherein the drive control unit is configured to control a direction of the movement of at least one of the supporting unit and the bed based on a position of the identified attachment unit.

17. The X-ray diagnosis apparatus according to claim 12, wherein the attachment unit includes a connector configured to transmit a signal related to the movement from the operation unit to the bed.

* * * * *